US008338175B2

(12) United States Patent
Devi et al.

(10) Patent No.: US 8,338,175 B2
(45) Date of Patent: Dec. 25, 2012

(54) CONJUNCTIVAL TISSUE SYSTEM

(75) Inventors: Kashyap Subhadra Devi, Navi Mumbai (IN); Kishore Reddy, Navi Mumbai (IN); Viraf Vasania, Navi Mumbai (IN)

(73) Assignee: Reliance Life Sciences Pvt. Ltd., Rabale, Navi, Mubai (IN)

( * ) Notice: Subject to any disclaimer, the term of this patent is extended or adjusted under 35 U.S.C. 154(b) by 1128 days.

(21) Appl. No.: 11/710,623

(22) Filed: Feb. 23, 2007

(65) Prior Publication Data

US 2007/0218039 A1    Sep. 20, 2007

(51) Int. Cl.
*C12N 5/00* (2006.01)
*C12N 5/02* (2006.01)

(52) U.S. Cl. ........ 435/377; 435/395; 435/401; 435/404; 435/405; 435/407; 435/408

(58) Field of Classification Search ........................ None
See application file for complete search history.

(56) References Cited

U.S. PATENT DOCUMENTS

| | | | |
|---|---|---|---|
| 6,152,142 | A | 11/2000 | Tseng |
| 6,610,538 | B2 | 8/2003 | DeLuca et al. |
| 6,921,665 | B2 | 7/2005 | McWhir et al. |
| 7,049,139 | B2 | 5/2006 | Tan et al. |
| 2002/0039788 | A1 | 4/2002 | Isseroff et al. |
| 2003/0208266 | A1 | 11/2003 | Tsai |
| 2005/0186672 | A1 | 8/2005 | Mahadeorao et al. |
| 2007/0166819 | A1 | 7/2007 | Ghosh et al. |
| 2007/0185014 | A1* | 8/2007 | Dartt ................................. 514/8 |

FOREIGN PATENT DOCUMENTS

| | | |
|---|---|---|
| EP | 0572364 | 12/1993 |
| WO | WO 00/73421 | 12/2000 |
| WO | WO 03/030959 | 4/2003 |
| WO | WO 03/093457 | 11/2003 |

OTHER PUBLICATIONS

Du et al. (2003) Functional reconstruction of rabbit corneal epithelium by human limbal cells cultured on amniotic membrane. Molecular Vision 9: 635-643.*
Meller et al. (1999) Conjunctival epithelial cell differentiation on amniotic membrane. Invest. Ophthalmol. Vis. Sci. 40: 878-886.*
Alison, Malcolm, et al., "Hepatic stem cells," Journal of Hepatology, 676-682, 29, 1998, USA.
Anderson, David F., et al., "Amniotic membrane transplantation for partial limbal stem cell deficiency," Br. J. Ophthalmol., 567-575, 85, 2001, GB.
Ang, Leonard P.K., et al., "Development of a Conjunctival Epithelial Equivalent with Improved Proliferative Properties Using a Multistep Serum-Free Culture System" Invest. Ophthalmol. Vis. Sci., 1789-1795, 45(6), 2004, USA.
Argueso, Pablo, et al., "Decreased Levels of the Goblet Cell Mucin MUC5AC in Tears of patients with Sjogren Syndrome," Invest. Ophthanol. Vis. Sci., 1004-1011, 43:4, 2002, USA.
Ausubel, et al., "Techniques for Mammalian Cell Tissue Culture," Current Protocols in Mol. Biol., Supplement 35, Appendix 3F, A.3F1-A.3F.10, 1996, USA.
Bahar, Irit, et al., "Pterygium Surgery, Fibrin Glue Versus Vicryl Sutures for Conjunctival Closure," Cornea, 1168-1172, 25:10, 2006, USA.
Belyakov, Oleg V., et al., "Biological effects in unirradiated human tissue induced by radiation damage up to 1 mm away," PNAS, 14203-14208, 102:40, 2005, USA.
Budak, Murat T., et al., "Ocular surface epithelia contain ABCG2-dependent side population cells exhibiting features associated with stem cells," Journal of Cell Science, 1715-1724, 118, 2005, USA.
Cotsarelis, George, et al., "Existence of Slow-Cycling Limbal Epithelial Basal Cells That Can Be Preferentially Stimulated to Proliferate: Implications of Epithelial Stem Cells," Corneal Epithelial Stem Cells, 201-209, USA.
Diebold, Yolanda, et al., "Characterization of epithelial primary cultures from human conjunctiva," Graefe's Arch Clin Exp Ophthalmol, 268-276, 234, 1997, USA.
Di Girolamo, Nick, et al., "Culture and characterisation of epithelial cells from human pterygia," Br J. Ophthalmol., 1077-1082, 83, 1999, GB.
Dua, Harminder S., "The conjunctiva in corneal epithelial wound healing," Br J. Ophthalmol, 1407-1411, 82, 1998, GB.
Dua, Harminder S., et al., "A new classification of ocular surface burns," Br J Ophthalmol, 1379-1383, 85, 2001, GB.
Dua, Harminder S., et al., "Limbal Stem Cells of the Corneal Epithelium," Survey of Ophthalmology, 415-425, 44:5, 2000, USA.
Gage, Fred H., "Mammalian Neural Stem Cells," Science, 1433-1438, 287, 2000.
Gilbard and Rossi, "Team Film and Ocular Surface Changes in a Rabbit Model of Neurotrophic Keratitis," Ophthalmology, 308-312, 97(3), 1990, USA.
Grueterich, Martin, et al., "Ex Vivo Expansion of Limbal Epithelial Stem Cells: Amniotic Membrane Serving as a Stem Cell Niche," Survey of Ophthalmology, 631-646, 48:6, 2003, USA.
Henderson, Timothy R.M., et al., "The long term outcome of limbal allografts: the search for surviving cells," Br. J. Ophthalmol., 604-609, 85, 2001, GB.
Holland, Edward J., "Epithelial Transplantation for the Management of Severe Ocular Surface Disease," Tr. Am. Ophth. Soc., 676-743, XCIV, 1996, USA.
Kessing, Svend Vedel, "Investigations of the Conjunctival Mucin (Quantitative studies of the goblet cells of conjunctiva)," ACTA Ophthalmologica, 439-453, 44, 1966.
Koizumi, Noriko, et al., "Amniotic Membrane as a Substrate for Cultivating Limbal Corneal Epithelial Cells for Autologous Transplantation in Rabbits," Cornea, 65-71, 19:1, 2000, USA.
Koizumi, Noriko, et al., "Cultivation of Corneal Epithelial Cells on Intact and Denuded Human Amniotic Membrane," Investigative Ophthalmology & Visual Science, 2506-2513, 41:9, 2000, USA.

(Continued)

*Primary Examiner* — Anne-Marie Falk
(74) *Attorney, Agent, or Firm* — Vinson & Elkins LLP

(57) ABSTRACT

The present disclosure describes a tissue system with conjunctival cells, including conjunctival stem cells. The conjunctival tissue system is derived from isolated tissue comprising conjunctival cells, and is suitable for restoring ocular surface impairments, particularly those that result from damaged or diseased conjunctiva. The tissue system is generated using a simple single medium culture scheme, and a support material, such as human amniotic membrane. The conjunctival tissue system generate is suitable for transplantation to treat the ocular surface of an eye of a subject that is damaged or diseased.

14 Claims, 4 Drawing Sheets

OTHER PUBLICATIONS

Koizumi, Noriko, et al., "Cultivated Corneal Epithelial Stem Cell Transplantation in Ocular Surface Disorders," Ophthalmology, 1569-1574, 108(9), 2001, USA.

Lemp, Michael A., et al., "The Precorneal Tear Film. I. Factors in Spreading and Maintaining a Continuous Tear Film Over the Corneal Surface," Arch Ophthal, 89-94, 83, 1970, USA.

Lindberg, Kristina, et al., "In Vitro Propagation of Human Ocular Surface Epithelial Cells for Transplantation," Invest Ophthamol Vis Sci., 2672-2679, 34:9, 1993, USA.

Lindstrom, Richard L., "Advances in Corneal Transplantation," The New England Journal of Medicine, 57-59, 315:1, 1986, USA.

McClosky, Kara E., et al., "Magnetophoretic Cell Sorting Is a Function of Antibody Binding Capacity," Biotechnol. Prog., 899-907, 19, 2003, USA.

Nakamura, Takahiro, et al., "The Successful Culture and Autologous Transplantation of Rabbit Oral Mucosal Epithelial Cells on Amniotic Membrane," Invest. Ophthalmol Vis. Sci., 106-116, 44:1, 2003, USA.

Ohno-Matsui, Kyoko, et al., "The effects of amniotic membrane on retinal pigment epithelial cells differentiation," Molecular Vision, 1-10, 11, 2005, USA.

Pellegrini, Graziella, et al., "Long-term restoration of damaged corneal surfaces with autologous cultivated corneal epithelium," The Lancet, 990-993, 349, 1997, GB.

Pellegrini, Graziella, et al., "Location and Clonal Analyisis of Stem Cells and Their Differentiated Progeny in the Human Ocular Surface," The Journal of Cell Biology, 769-782, 145:4, 1999, USA.

Pfister, Roswell R., "Chemical Injuries of the Eye," Ophthalmology, 1246-1253, 90, 1983, USA.

Pfister and Sommers, "Fibrin Sealant in Corneal Stem Cell Transplantation," Cornea, 593-598, 24:5, 2005, USA.

Pittenger, Mark F., et al., "Multilineage Potential of Adult Human Mesenchymal Stem Cells," Science, 143-147, 284, 1999, USA.

Potten, Christopher S., "Stem cells in gastrointestinal epithelium: numbers, characteristics and death," Phil. Trans. R. Soc. Lond. B., 821-830, 353, 1998, GB.

Prabhasawat, Pinnita, et al., "Impression Cytology Study of Epithelial Phenotype of Ocular Surface Reconstructed by Preserved Human Amniotic Membrane," Arch Ophthalmol., 1360-1366, 115, 1997, USA.

Schermer, Alexander, et al., "Differentiation-related Expression of a Major 64K Corneal Keratin in Vivo and in Culture Suggests Limbal Location of Corneal Epithelial Stem Cells," The Journal of Cell Biology, 49-62, 103, 1986, USA.

Shatos, Marie A., et al., "Isolation and Characterization of Cultured Human Conjunctival Goblet Cells," Investigative Ophthalmology & Visual Science, 2477-2486, 44:6, 2003, USA.

Shatos, Marie, et al., "Isolation, Characterization, and Propagation of Rat Conjunctival Goblet Cells in Vitro," Invest. Ophthalmology & Vis. Sci., 1455-1464, 42:7, 2001, USA.

Shimazaki, Jun, et al., "Transplantation of Human Limbal Epithelium Cultivated on Amniotic Membrane for the Treatment of Severe Ocular Surface Disorders," Ophthalmology, 1285-1290, 109:7, 2002, USA.

Shimazaki, Jun, et al., "Amniotic Membrane Transplantation for Ocular Surface Reconstruction in Patients with Chemical and Thermal Burns," Ophthalmology, 2068-2076, 104, 1997, USA.

Tan, Donald T.J., et al., "Limbal Transplantation," Ophthalmology, 29-36, 103, 1996, USA.

Tan, Donald T.H., et al., "Reconstruction of the Ocular Surface by Transplantation of a Serum-Free Derived Cultivated Conjunctival Epithelial Equivalent," Transplantation, 1729-1734, 77:11, 2004, USA.

Tsai, Ray Jui-Fang, et al., "Conjunctival Epithelial Cells in Culture-growth and Goblet Cell Differentiation," Progress in Retinal and Eye Research, 227-241, 16:2, 1997, USA.

Tsai, Ray Jui-Fang, et al., "The Effects of Fibroblasts on the Growth and Differentiation of Human Bulbar Conjunctival Epithelial Cells in an in Vitro Conjunctival Equivalent," Invest Ophthalmology & Vis. Sci., 2865-2875, 35:6, 1994, USA.

Tsai, Ray Jui-Fung, et al., "Comparison of Limbal and Conjunctival Autograft Transplantation in Corneal Surface Reconstruction in Rabbits," Ophthalmology, 446-455, 97, 1990, USA.

Tsai, Ray Jui-Fung, et al., Reconstruction of Damaged Corneas by Transplantation of Autologous Limbal Epithelial Cells, N. Eng J Med., 86-93, 343, 2000, USA.

Tseng, Scheffer C.G., et al., "Amniotic Membrane Transplantation with or without Limbal Allografts for Corneal Surface Reconstruction in Patients with Limbal Stem Cell Deficiency," Arch Ophthalmol., 431-441, 116, 1998, USA.

Tseng, Scheffer C.G., et al., "Amniotic Membrane Transplantation for Conjunctival Surface Reconstruction," American J. of Ophthalmology, 1997, 765-774, 124(6).

Tseng, Scheffer C.G., et al., "Possible Mechanisms for the Loss of Goblet Cells in Mucin-deficient Disorders," Ophthalmology, 545-552, 91:6, 1984, USA.

Tseng, Scheffer C.G., "Regulation and clinical implications of corneal epithelial stem cells," Molecular Biology Reports, 47-58, 23, 1996, USA.

Watt, Fiona M., "Epidermal stem cells: markers, patterning and the control of stem cell fate," Phil. Trans. R. Soc. Lond. B, 831-837, 353, 1998, GB.

Wei, Zhi-Gang, et al., ,,In Vitro Growth and Differentiation of Rabbit Bulbar, Fornix, and Palpebral Conjunctival Epithelia, Investigative Ophthalmology & Vis. Sci., 1814-1828, 34:5, 1993, USA.

Weissman, Irving L., "Translating Stem and Progenitor Cell Biology to the Clinic: Barriers and Opportunities," Science, 1442-1446, 287, 2000, USA.

Zieske, James, D., "Perpetuation of Stem Cells in the Eye," Eye, 163-169, 8, 1994, USA.

* cited by examiner

CONJUNCTIVAL TISSUE SYSTEM

CROSS-REFERENCES TO RELATED APPLICATIONS

This application claims priority to Indian Application No. 267/MUM/2006, filed on Feb. 24, 2006, which is entirely incorporated by reference herein for all purposes.

STATEMENT REGARDING FEDERALLY SPONSORED RESEARCH OR DEVELOPMENT

Not applicable.

INCORPORATION-BY-REFERENCE

The Sequence Listing file "11710623SeqListing_ST25.txt" is hereby incorporated by reference into the present specification in its entirety.

REFERENCE TO A "MICROFICHE APPENDIX"

Not applicable.

BACKGROUND OF THE INVENTION

1. Field of the Invention

The present disclosure relates to tissue systems, methods of producing tissue systems and methods of treatment using tissue systems comprising conjunctival cells for restoring damaged or diseased ocular surfaces. The tissue system of the present disclosure comprises mammalian conjunctival cells, preferably progenitor conjunctival cells derived from the fornix region of the conjunctiva. The present disclosure in particular relates to the culturing of progenitor conjunctival cells on a suitable support material such as amniotic membrane under controlled culture conditions.

2. Description of Related Art

Stem cells are responsible for cellular replacement and tissue regeneration throughout the life of an organism. Stem cells are unspecialized cells that give rise to specialized cells, and have extensive proliferation potential. Depending on the type of stem cell, these cells may differentiate into several cell lineages and/or repopulate a tissue upon transplantation. Embryonic stem (ES) cells are quintessential stem cells with unlimited self-renewal and pluripotent potential, and are derived from the inner cell mass of a blastocyst-stage embryo. Adult stem cells are specialized undifferentiated stem cells, which, after birth and throughout adulthood, retain the ability to replace cells and regenerate tissues in an organism. It is generally understood that adult stem cells, as compared to ES cells, have less self-renewal ability, and although they may differentiate into multiple lineages, are not generally described as pluripotent. Cell therapy has the potential to treat any disease that is associated with cell dysfunction or damage, including but not limited to the potential for manipulating stem cells, whether ES cells or adult stem cells, to repair or replace diseased or damaged tissue. This potential has generated a great deal of excitement in the scientific, medical, and biotechnology communities.

Adult stem cells (also referred to as "tissue-specific stem cells") have been found in various tissues of the adult body, including bone marrow (Weissman, Science 287:1442-1446, 2000), neural tissue (Gage, Science 287:1433-1438, 2000), gastrointestinal tissue (Potten, Phil Trans R Soc Lond. B. 353:821-830, 1998), epidermal tissue (Watt, Phil Trans R Soc Lond B. 353:831, 1997), hepatic tissue (Alison and Sarraf, J Hepatol. 29:678-683, 1998), and mesenchymal tissue (Pittenger et al., Science 284:143-147, 1999). Adult stem cells that are found in the corneoscleral limbus of the mammalian eye are essential for the maintenance of a healthy ocular surface, and participate in the dynamic equilibrium of healthy ocular and corneal surfaces.

The surface of the eye consists of the cornea, the conjunctiva, and the border between the two, which is known as the corneoscleral junction, or limbus. The optical surface has two basic epithelial surfaces, corneal epithelium and conjunctival epithelium. The conjunctiva is a two to three layer epithelium that extends from the mucocutaneous junction, beginning at the eyelashes on to the inner surface of the eyelids, over the ocular surface on the eye proper and ending at the limbus. Stem cells that continually replace conjunctival epithelium have been shown to reside at the conjunctival fornix. Wei et al., Invest Ophthalmol Vis Sci. 34:1814-28, 1993. These stem cells, which lie at the uppermost and lowermost regions of the conjunctiva at the forniceal junction between the sclera and the eyelids, are known as conjunctival stem cells or progenitor conjunctival cells.

A major role of the conjunctiva is to provide ocular surface hydration and lubrication through the production of tears by mucin-producing goblet cells, which are highly specialized epithelial cells that are interspersed between the conjunctival epithelial cells. Mucins are highly glycosylated proteins secreted primarily by goblet cells present in the conjunctiva. The conjunctival surface integrity is influenced by the level of ocular mucin that is secreted by goblet cells. Mucin production is the main characteristic feature of conjunctival cells. The multiple layers of stratified conjunctival epithelium along with the interspersed goblet cells together are continuously regenerated maintaining the functional integrity of the ocular surface (Kessing, S V, Acta Ophthalmol 44:439-453, 1966; Lemp, et al., Arch Ophthalmol. 83:89-94, 1970).

Mucin deficiency is detected in alkali burns, chemical and thermal burns, Stevens-Johnson Syndrome (SJS), neurotrophic keratitis and Ocular Cicatricial Pemphigoid (OCP). See Gilbard and Rossi, Ophthalmol. 97:308-312; 1990; Lemp, Int Ophthalmol Clin. 13:185-189, 1973; Tseng et al., Ophthalmol. 91:545-552, 1984. The conjunctiva also provides a smooth and wet cellular surface to support the tear film on the corneal surface, which in turn results in an optically clear optical surface and clear vision. Thus, the conjunctiva supports the health of the corneal epithelium. Because the corneal epithelium is dependent on a healthy conjunctival surface to maintain clear vision, many ocular surface diseases initiate with conjunctival damage, followed by secondary limbal and corneal damage. Stratifying epithelia are self-renewing tissues that undergo constant reorganization, necessitated by a continuous loss of terminally differentiated superficial cells, balanced by basal cell proliferation. Therefore, in order to maintain a healthy epithelial structure, a critical balance between cell proliferation and differentiation must be achieved at all times.

Tissue culture techniques have been widely employed for stratified epithelia such as epidermis and cornea to begin to identify those factors that may be important during keratinocyte proliferation and maturation. Researchers in this area have utilized rabbit or bovine conjunctival epithelial cells in culture, and several models for the culture of normal human conjunctival keratinocytes have been developed. Primary human conjunctival keratinocytes have been propagated in long-term culture from cadaver eyes using serum containing culture medium and, in some cases, a fibroblast feeder layer.

Lindberg et al., Invest Ophthalmol Vis Sci. 34:2672-2679, 1993; Tsai et al., Invest Ophthalmol Vis Sci. 35:2865-2875, 1994.

In the clinical context of ocular injuries, conjunctival involvement has been estimated by dividing the bulbar and forniceal conjunctiva into quadrants and determining the area involved. The involvement of the bulbar and forniceal conjunctiva is considered significant for the eventual outcome after ocular injury or disease. Argüeso et al., Invest Ophthalmol Vis Sci. 43:1004-1011, 2002; Dua et al., Br J Ophthalmol. 85:1379-1383, 2001; Pfister, Opthalmology 90:1246-53, 1983. For example, in grade 4, 5 and 6 ocular burns, in which the surviving corneal and conjunctival epithelium is thin to absolutely zero, the desirable ocular management may be to attempt a restorative and reconstructive intervention by re-establishing both corneal and conjunctival epithelial cover, one after the other (see Dua, Br J Opthalmol. 82: 1407-11, 1998). In Nakamura et al., Invest Ophthalmol Vis Sci 44(1): 106-116, 2003, re-establishment of the corneal mileu was attempted by transplanting cultured limbal stem cells on human amniotic membrane (HAM) with good prognosis. See also Shimazaki et al., Ophthalmology 109(7):1285-1290, 2003; Tseng et al., Arch Ophthalmol. 116:431-41, 1998; Koizumi et al., Ophthalmology 108(9):1569-1574, 2001. There are also reports in the literature on conjunctival autografts and culturing progenitors from bulbar and forniceal regions on HAM (see Grueterich et al., Surv Ophthalmol. 48(6):631-46, 2003; Wei et al., Invest Ophthalmol Vis Sci. 34:1814-1828, 1993).

With respect to conjunctival tissue equivalents, U.S. Pat. No. 7,049,139 discloses culturing conjunctival cells on HAM in a multi-step process using three different media to produce a conjunctival tissue equivalent. The three different steps used to prepare the tissue equivalent include culturing the conjunctival cells in a primary culture media, a proliferative culture media, and a differentiative culture media. Two of the three media types disclosed include cholera toxin as one of the ingredients of the medium. Cholera toxin, which is a potential carcinogen, can cause eye irritation. The multi-step process was used to enhance the stability of the tissue equivalent for clinical transplantation. The efficiency of a conjunctival tissue equivalent cultivated in serum-free conditions on HAM was studied after the graft was transplanted in seven patients with different conjunctival surface disorders. Epithelisation and graft integrity was studied. Tan et al., Transplantation 77(11):1729-1734, 2004. See also, Tan et al., U.S. Pat. No. 7,049,139; Ang et al., (2004) Invest Ophthalmol Vis Sci. 45 (6):1789-1795. U.S. Pat. No. 7,049,139 requires three steps to produce a conjunctival tissue equivalent, using a culturing media, a proliferation media, and a differentiation media. The media employed for differentiation includes a high calcium concentration, as well as choleratoxin.

Most studies of tissue equivalents or tissue systems have focused on the ability to reconstitute a tissue equivalent that bears the structural and functional characteristics of the tissue of origin. This has been achieved by differentiating cells in culture, for example, by modifying the culture conditions and air-lifting. Terminally differentiated cells have limited long-term proliferative capacity, however, which results in a lower regenerative potential after transplantation. In addition, the use of epithelial tissue constructs for ocular surface transplantation requires that cells be sufficiently attached to the underlying substrate so that they are not sloughed off by direct mechanical or shearing forces, during or after surgical transplantation. Therefore, a delicate balance is necessary to preserve the proliferative potential of transplanted cells, while at the same time ensuring that transplanted cells have the necessary functional characteristics of the tissue organ. The ideal tissue construct is one in which transplanted cells possess a long-term regenerative capability for cellular renewal and replacement of tissue.

While tissue equivalents developed may be transplanted by conventional methods, for example suturing the graft onto the eye, this can cause discomfort to the recipient. Further, the act of suturing requires more precision then a suture-less method, since the site of the diseased or damaged eye cannot be clearly visualized. In addition, such transplantations usually leave a scar at the site. Thus, a suture-less transplantation would be preferred over conventional methods necessitates the development of other techniques or cell-based membrane delivery systems that can adhere to the site of transplantation without suture. Pfister and Sommers, Cornea 24(5):593-598, 2005, found that fibrin sealant alone can attach corneal stem cell transplants to the limbal niche.

In response to the need for a more desirable conjunctival tissue equivalent, the present disclosure describes a tissue system with a long-term regenerative capability for cellular renewal and replacement of damaged or diseased tissue on the ocular surface. A particular advantage of the presently disclosed conjunctival tissue system is that it involves a relatively simple culture scheme, in that it employs a single media used for culturing, expansion and differentiation of the conjunctival tissue system, and can avoid the use of toxins such as choleratoxin and high calcium concentration. This simple culturing scheme may minimize contamination problems in cGMP facilities. In addition, the conjunctival tissue system disclosed herein may be introduced onto the ocular surface using a suture-less method.

BRIEF SUMMARY OF THE INVENTION

The present disclosure describes a tissue system comprising conjunctival cells cultured on an appropriate support material, such as a biocompatible membrane or extracellular matrix, as well as methods for preparing such a conjunctival tissue system. In preferred embodiments, the conjunctival cells are cultured on amniotic membrane, such as human amniotic membrane (HAM), to generate the conjunctival tissue system. Preferably, the conjunctival tissue system disclosed herein is an equivalent of conjunctival tissues on the ocular surface. Surprisingly, the conjunctival tissue system disclosed herein, which may be prepared by culturing a conjunctival biopsy in a single medium, is sufficiently stable, stratified, and adherent that it can be used for clinical transplant. Preferably, the stable conjunctival tissue system is less likely to break apart after being introduced to the eye of the recipient, thereby increasing the clinical success of this method, as well as reducing the recovery time for the recipient.

The method for preparing a conjunctival tissue system comprises a single culturing medium to culture conjunctival cells, thereby providing a simple system for generating the desired conjunctival tissue system. In a preferred embodiment, a single-step culture media is able to generate a multi-layered tissue system comprising conjunctival cells. Preferably, the conjunctival tissue system has a stratified squamous epithelium comprising several layers of conjunctival cells. In other preferred embodiments, the conjunctival tissue system comprises several layers of conjunctival cells connected by one or more desmosome structures formed between adjacent cells in each layer. The conjunctival tissue system may also comprise apical microvilli, intercellular junctions, and/or a normal cytoskeleton. In other embodiments, the conjunctival tissue system may be generated by culturing the conjunctival cells on a support material such as HAM using a simple culture scheme with glass slides.

As used herein, conjunctival cells may be progenitor conjunctival cells, differentiated conjunctival cells, or any combination of the two cell types. In certain embodiments, the tissue system comprises progenitor conjunctival cells, wherein at least about 20-90% of the cells in the tissue system are progenitor conjunctival cells. Preferably, the tissue system comprises at most about 20% terminally-differentiated cells. In other embodiments of the present disclosure, the conjunctival tissue system is transplanted to a site of damage or disease on the ocular surface, for example the conjunctiva, to treat and/or restore the conjunctival surface at the site. In certain embodiments, the engrafted cells migrate away from the transplant site into the cellular structure of the recipient, which aids in the treatment or restoration of the optical surface. In other embodiments, treatment with the conjunctival tissue equivalent resolves the underlying disease and/or maintains conjunctival epithelialization, without significant complications. Preferably the integrity of the conjunctival tissue system is maintained as needed, and remains well-epithelialized after surgery. A preferred clinical outcome is a good functional and cosmetic result in the treated eye.

In various embodiments, the conjunctival cells found in the tissue system express one or more stem cell marker genes such as, for example, Oct-4. Preferably about 30-35% of the cells in the conjunctival tissue system are Oct-4-positive. In other embodiments, the conjunctival tissue system comprises conjunctival cells that are positive for cytokeratin markers such as AE1, AE3, cytokeratin-4 (K4), cytokeratin-7 (K7), and cytokeratin-19 (K19). The keratins are a family of intermediate filament cytoplasmic proteins expressed by epithelial cells. Cytokeratins AE-1 and AE-3 are markers for characteristic intermediate filament proteins of epithelial cells. Cytokeratin K4 is a marker for non-keratinized, stratified epithelia. In certain embodiments, the conjunctival tissue system comprises conjunctival cells that are positive for mucin markers such as MUC5AC and MUC4. In still other embodiments, cells in the tissue system express cell-specific markers such as P63. The present disclosure also provides for the molecular and cellular characterization of the conjunctival cells present in the tissue system using one or more of the above markers. In some embodiments, about 1%, 2%, 3%, 4%, 5%, 10%, 15%, 20%, 30%, 40%, 50%, 60%, 70%, 80% or 90% of the cells in the conjunctival tissue system express AE1, AE3, K4, K7, and/or K19. Preferably, the conjunctival tissue system of the present disclosure also comprises goblet cells. The goblet cell density in the disclosed tissue system may be about 2.5±1.1 goblet cells per 100 cells. In preferred embodiments of the present disclosure, the tissue system comprises viable progenitor conjunctival cells, for example in the range of about 2 to 2.5 million cells in the tissue system. The number of progenitor conjunctival cells present in the tissue system may be increased or decreased depending on the needs of the recipient. The density range of cells may vary according to patient need; for example, the range administered to the patient may be between $1 \times 10^6$, $1.5 \times 10^6$, and $2 \times 10^6$ to $2.5 \times 10^6$ cells per culture.

In various embodiments, the present disclosure provides a tissue system comprising a support material for delivery of conjunctival cells. The support material may also comprise an appropriate biocompatible membrane, such as amniotic membrane (e.g., HAM). The tissue system of the present disclosure preferably involves culturing conjunctival cells on a biocompatible membrane which is suitable for use in the eye, and which does not interfere with the normal wound healing process.

Although the conjunctival tissue system disclosed herein may be transplanted to the appropriate site of the eye using methods well known in the art, the present disclosure also describes a suture-less method for delivering the tissue system to the eye of a subject. In the present disclosure, the terms "subject," "patient," and "recipient" are used interchangeably. In a preferred embodiment, the disclosure provides a suture-less delivery method for the conjunctival tissue system to the ocular surface of the eye of a subject. In certain embodiments, the tissue system uses a tissue adhesive or a biocompatible glue for adhering the tissue system of the present disclosure to the eye of the recipient. In some embodiments, the biocompatible glue comprises Amcrylate or fibrin sealant. In a preferred embodiment, the biocompatible glue is a sterile tissue adhesive selected from polylactic acid, polylactide glycolic acid, copolymers of polylactic acid and acrylates, and any combinations thereof. In other embodiments, the biocompatible glue comprises any adhesive which is biocompatible to the eye of the subject. The use of a biocompatible glue may be neat and less cumbersome, as well as safer than sutures, so that the cultured conjunctival transplant may be set on the injury with minimal disturbance to the recipient's eye, and with integration of at least some of the transplanted cells.

BRIEF DESCRIPTION OF THE SEVERAL VIEWS OF THE DRAWINGS

The following drawings form part of the present invention and are included to substantiate and demonstrate the important aspects of the disclosure. The present invention may be better understood by the following drawings in combination with the detailed description of the specific embodiments presented herein.

FIG. 1A a shows three-days-old culture of conjunctival cells obtruding the HAM. FIG. 1B shows a 14-days-old confluent culture of cells on HAM. FIG. 1C shows immunofluorescence staining with cytokeratin AE-1 on the culture section. FIG. 1D shows immunofluorescence staining with cytokeratin AE-3 on the culture section. FIG. 1E shows PAS staining of the whole mount of a 20-days-old culture. The PAS stains goblet cells magenta.

FIG. 3A shows a rabbit's normal eye. FIG. 3B shows saturated NaOH filter paper placed on the rabbit's conjunctiva. FIG. 3C shows the injury site just before the transplantation. FIGS. 3D and 3E show the transplanted site. FIG. 3F shows the healed injury. FIG. 3G shows a control eye with injury made and followed up, showing traces of injury.

FIG. 4A shows a normal rabbit conjunctiva section stained with PAS (to detect goblet cells). The goblet cells stain magenta. FIG. 4B shows the injury site, which shows no goblet cells and the epithelium sloughed off. FIG. 4C shows wound healing without epithelium in the eye when only HAM is transplanted onto the eye. FIG. 4D shows wound healing in the eye with only injury and no transplant. FIG. 4E shows haematoxylin and eosin (H&E) staining of the site of injury after transplantation of a tissue system with cultured conjunctival cells. FIG. 4F shows PAS staining of the engrafted human and rabbit cells at the site of transplantation. FIGS. 4G and 4H show anti-human-mitochondrial-antibody-positive brown colored human cells detected at the site of transplantation. FIG. 4I shows human cells that migrated to the sub-epithelial zone of the rabbit's conjunctiva.

DETAILED DESCRIPTION OF THE INVENTION

Figure 1:
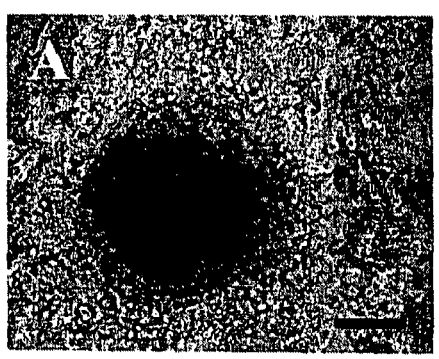
FIG. 1: Characterization of conjunctival cell culture on HAM.
Figure 1:
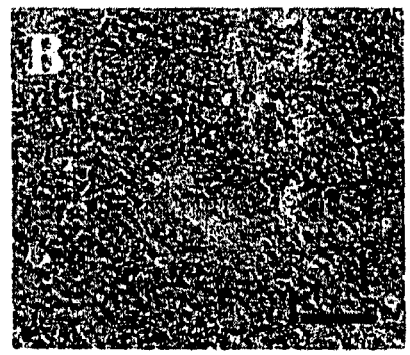
Figure 1:
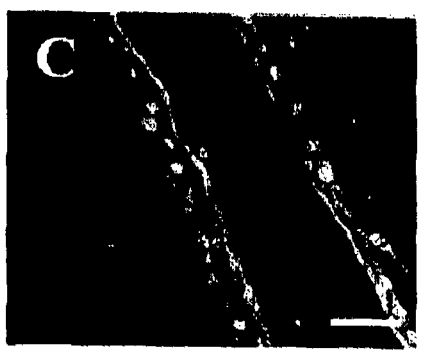
Figure 1:
Figure 1:

The present disclosure is directed to a novel method of treating the destruction of conjunctival epithelium, whether by damage or disease, through treatment with a tissue system comprising conjunctival cells, i.e., progenitor conjunctival cells, differentiated conjunctival cells, or a combination thereof. Preferably, the conjunctival tissue system also comprises goblet cells, which are characterized as being ellipsoid in shape and containing large secretory granules containing mucin. The present disclosure specifically addresses the isolation, expansion, and generation of a conjunctival tissue system. In preferred embodiments, the conjunctival tissue system restores the functional integrity of the conjunctiva of the recipient of the tissue system. Preferably, the conjunctival tissue system disclosed herein is cultured from a tissue that comprises conjunctival cells (e.g., a biopsy or explant) using a simple single-step method, in which the cells are expanded ex vivo to form a conjunctival tissue equivalent. It is surprising that such a method can produce a tissue culture with the stability necessary for clinical transplant. For example, the conjunctival tissue system comprises cell-to-cell and cell-to-substrate adhesion structures that ensure structural integrity after surgical manipulation and transplantation. The single-step method preferably utilizes media that is able to support the outgrowth of the cells in the conjunctival biopsy or explant, the expansion of conjunctival cells, including progenitor conjunctival cells, as well as the formation of a tissue system which can be used to treat diseased or damaged conjunctiva. In certain embodiments, the single-step method may also support the appropriate level of terminal differentiation of cells in the tissue system. In addition, the present disclosure describes a novel method of delivering a conjunctival tissue system to the optical surface of a patient using a tissue adhesive or a biocompatible glue.

In preferred embodiments, the conjunctival tissue system of the present disclosure is used to therapeutically treat subjects with ocular damage or disease, particular ocular surface impairments of the conjunctiva. The damage to the eye may be caused by injury or trauma. As used herein, a "conjunctival tissue system" is a population of cells comprising conjunctival cells on an appropriate support material, preferably suitable for transplantation to a mammalian subject. Preferably, the conjunctival tissue system disclosed herein is an equivalent of conjunctival tissues on the ocular surface. In preferred embodiments, the tissue system is a transplant, for example a surgical graft or a composite graft, with multi-layered aggregates of cells. The terms "transplant," "transplanting," "transplanted" or "transplantation" are used interchangeably herein with the terms "implant," "implanting," "implanted," "implantation," "graft," "grafted," or "grafting." While the conjunctival cells, whether progenitor cells or differentiated cells, may be obtained from any suitable mammal, human tissue is a particularly preferred source.

The conjunctival tissue system disclosed herein may be used to treat a subject with conjunctival damage or disease, for example by restoring ocular surface hydration and lubrication. In preferred embodiments, the conjunctival tissue system restores mucin-producing goblet cells at the site of injury or disease, thereby improving lubrication through tearing. Preferably, the conjunctival tissue system will function in the subject to restore a smooth and wet cellular surface to support the tear film on the corneal surface, thereby improving vision. In preferred embodiments, the conjunctival tissue system is able to restore a healthy conjunctiva which supports the corneal epithelium. Therefore, the conjunctival tissue system disclosed herein may be used not only to treat damaged or diseased conjunctival epithelium, but also may prevent secondary corneal and limbal damage, thereby potentially preventing secondary limbal stem cell deficiency. Treatment with a conjunctival tissue system as disclosed herein preferably results in little or no neovascularization, chronic inflammation, recurrent epithelial defects, or stromal scarring.

In preferred embodiments, the conjunctival tissue system disclosed herein may be used to treat alkali burns, chemical and thermal burns, Stevens-Johnson Syndrome (SJS), neurotrophic keratitis, Ocular Cicatricial Pemphigoid (OCP), conjunctival reconstruction after eye surgery such as pterygium excision, glaucoma surgery (e.g., trabeculectomy or secton surgery), retinal detachment and squint surgery, conjunctival nevus, persistent leaking trabeculectomy blebs, superior limbic keratoconjunctivitis, and other ocular surface disorders or injury in which the conjunctiva is damaged. The conjunctival tissue system may also be used to treat a site with mucin deficiency. In certain embodiments, the therapeutic application of the conjunctival tissue system disclosed herein to treat an ocular surface disorder may be combined with a second therapeutic treatment to treat corneal damage and/or limbal stem cell deficiency, for example as disclosed in U.S. Ser. No. 11/043,019, which is incorporated herein by reference in its entirety. The therapeutic application of the conjunctival tissue system may precede any therapeutic treatment of a limbal stem cell deficiency by varying periods of time, for example by days, weeks, months, or years.

"Conjunctival progenitor cells," "progenitor conjunctival cells", and "conjunctival stem cells" are used interchangeably herein, and are precursor cells or stem cells of the conjunctiva of the eye. The location and distribution of the conjunctival progenitor cells have been shown to be in the fornix region of conjunctiva in mice and rabbits (Diebold et al., Graefes Arch Clin Exp Opthalmol 235:268-276, 1997; Pellegrini et al., J Cell Biol 145(4):769-782, 1999). These progenitor cells appear to be found primarily at the uppermost and lowermost regions of the conjunctiva at the forniceal junction between the sclera and the eyelids. It is also thought that mucin-producing goblet cells, which are interspersed between the conjunctival epithelial cells on the conjunctival surface, are also derived from conjunctival progenitor cells.

In preferred embodiments, the conjunctival tissue system comprises progenitor conjunctival cells, wherein at least about 20-90% of the cells in the tissue system are progenitor conjunctival cells. Preferably, the progenitor conjunctival cells comprise at least about 20%, 30%, 40%, 50%, 60%, 70%, 80%, 90%, 95% or 99% of the cells in the tissue system. In other embodiments, the conjunctival tissue system comprises no more then about 20% terminally-differentiated cells. Preferably, the conjunctival tissue system comprises at most about 50%, 40%, 30%, 20%, 15%, 10% or 5% terminally-differentiated cells, including but not limited to differentiated conjunctival cells.

In various embodiments, the conjunctival cells found in the tissue system express one or more stem cell marker genes such as, for example, Oct-4, p63, and Connexin 43. Preferably the conjunctival tissue system comprises about 10-20%, 20-30%, 30-35%, 40-45%, or 45-50% Oct-4-positive cells. In other embodiments, the conjunctival cells in the tissue system are positive for cytokeratin markers such as AE1, AE3, K4, K7, and K19, and mucin markers such as MUC5AC and MUC4. In certain embodiments, about 5%, 10%, 20%, 30%, 40%, 50%, 60%, or 70% of the cells in the conjunctival tissue system are AE1-positive cells, AE3-positive cells, K4-positive cells, K7-positive cells, K19-positive cells, MUC5AC-positive cells, and/or MUC4-positive cells. In preferred embodiments, the conjunctival tissue system comprises about 75-80% P63-positive cells, and about 30-35% Oct-4-positive cells. In other embodiments, cells in the tissue system express one or more cell-specific markers such as, for example, P63, Oct-4, Connexin 43, and ABCG2 (Budak et al., J Cell Sci. 118:1715-24, 2005). Preferably the conjunctival tissue system comprises about 40-45%, 45-50%, 50-55%, 55-60%, 60-65%, 65-70%, 70-75%, 75-80%, 80-85%, 85-90%, or 90-95% P63-positive cells. P63 and Oct-4 are markers for progenitor conjunctival cells, and the presence of the these markers in the cultured cells demonstrates a mixed population of progenitor cells and differentiated cells, which, at the preferred ranges, results in no more than about 20% terminally-differentiated cells in the tissue system.

In preferred embodiments of the present disclosure, the conjunctival tissue system comprises goblet cells. The goblet cell density in the disclosed tissue system may be about 1, 1.5, 2, 2.5, 3, 3.5, 4, 4.5, or 5 goblet cells per 100 cells. In certain embodiments, the tissue system comprises about 0.5%, 1%, 2%, 3%, 4%, 5%, 6%, 7%, 8%, 9%, 10%, 15%, 20%, or more goblet cells. In preferred embodiments of the present disclosure, the tissue system comprises viable progenitor conjunctival cells, for example in the range of about 2.0 to 2.5 million cells in the tissue system. In other embodiments, the range of progenitor conjunctival cells in the tissue system is from about 0.5 to 1.0 million cells, 1.0 to 1.5 million cells, 1.5 to 2.0 million cells, 2.5 to 3.0 million cells, or 3.0 to 3.5 million cells. The number of progenitor conjunctival cells present in the tissue system may be increased or decreased depending on the needs of the recipient. Preferably the tissue system comprises about 20%, 30%, 40%, 50%, 60%, 70%, 80%, 85%, 90% or 95% viable progenitor conjunctival cells. In some embodiments, the conjunctival tissue system comprises about 1-5%, 5-10%, 10-15%, 15-20%, 20-25%, 25-30%, 30-35%, 35-40%, 40-45%, 45-50%, or 50-55% K4-positive cells. In other embodiments, the conjunctival tissue system comprises about 1-5%, 5-10%, 10-15%, 15-20%, 20-25%, 25-30%, 30-35%, 35-40%, 40-45%, 45-50%, or 50-55% K7-positive cells. In still other embodiments, the conjunctival tissue system comprises about 1-5%, 5-10%, 10-15%, 15-20%, 20-25%, 25-30%, 30-35%, 35-40%, 40-45%, 45-50%, or 50-55% K19-positive cells. Preferably, the conjunctival tissue system does not comprise cells, or comprises only a small percentage of cells that express keratin K12. In other embodiments, the conjunctival tissue system disclosed herein is transparent and lacks a cornified striatum on its surface. Preferably the conjunctival tissue system comprises few if any cells that express cytokeratin K3, a corneal-specific cytokeratin (Schermer et al., J Cell Biol 103:49-62, 1986).

The presence of a large population or high percentage of conjunctival progenitor cells in the tissue system greatly facilitates the ability of the tissue system to restore damaged or diseased ocular surfaces after transplantation to a mammalian subject. In addition, the high proportion of conjunctival progenitor cells in the tissue system allows the system to be stable for a longer period of time by continuously repopulating the ocular surface with viable conjunctival progenitor cells, which are essential to the healthy functioning of the ocular surface. In certain embodiments, the tissue system is a composite graft comprising an extracellular matrix, for example, amniotic membrane (e.g., HAM), having a plurality of conjunctival progenitor cells and terminally differentiated cells, wherein the plurality of conjunctival progenitor cells are cultured ex vivo on the extracellular matrix. In other embodiments, the tissue system comprises conjunctival cells on biocompatible polymers. In still other embodiments, the conjunctival cells are grown on artificial substrates that can support epithelial tissue. Preferably the substrates used to support the growth of conjunctival cells, and the formation of the tissue system, promote tissue stratification. In certain embodiments, the substrates may also support terminal differentiation.

In preferred embodiments, the donor of the conjunctival cells used to generate the conjunctival tissue system is also the recipient of the tissue system transplant (i.e., autologous tissue system). Alternatively, the donor of the conjunctival tissue biopsy may not be the recipient of the conjunctival tissue system (i.e., heterologous tissue system). In a heterologous tissue system, preferably the donor is a bio-compatible donor, for example a close relative of the recipient, or the biopsy may also be from a bio-compatible (e.g., histocompatible) cadaver (i.e., allogenic tissue system). It is generally desirable that transplanted cells or tissues be genetically identical to the recipient of the transplant in order to avoid problems with tissue rejection.

In order to generate the tissue system disclosed herein, first a biopsy comprising conjunctival cells, or alternatively conjunctival cells isolated through methods well known to those of skill in the art, must be collected or isolated. The conjunctival tissue used to generate the tissue system may be isolated from any suitable mammal, with human tissue as a particularly preferred source. For example, conjunctival tissue may be isolated from the forniceal region of the human eye, e.g., the forniceal conjunctiva. Preferably conjunctival progenitor cells are cultured from such isolated tissue. The tissue system generated according to the methods disclosed herein should be suitable for transplantation to a recipient, particularly a recipient with a mucin deficiency, or other injury or disease, in one or both eyes. In other preferred embodiments, the recipient and donor are the same.

An advantage of using conjunctival tissue as the source to derive a tissue system as disclosed herein is the relative ease in obtaining conjunctival tissue from a donor. Another advantage is that obtaining the biopsy should pose minimal risk of any subsequent corneal or limbal damage. The process requires only minor surgery that is safe, simple, and efficient, and only small biopsies of conjunctival tissue are needed. The process is carried out under aseptic conditions, as well as under local anesthetic. Preferably the biopsy is isolated from the region high up in the superior conjunctival fornix, or deep below in the inferior conjunctival fornix. These locations provide a maximal density of progenitor conjunctival cells. Human conjunctival biopsy specimens may be obtained, for example, from patients undergoing routine surgery for nasal pterygium (Girolamo et al., Br J Ophthalmol. 83:1077-1082, 1999) or cataract. To obtain a biopsy, a small piece of normal conjunctiva (e.g., 1×3 mm size) may be removed from the superior bulbar region, 10 to 15 mm from the limbus. A second similarly sized biopsy may also be obtained to provide an additional and alternative source of conjunctival cells. Conjunctival biopsies are collected to generate the conjunctival tissue system, for example 2 or more weeks prior to transplant of the tissue system. After the biopsy is isolated, it may be dissected free of the underlying stroma, and placed into transport media and sent to the laboratory for preparation of the tissue system.

After removal of the tissue comprising conjunctival cells from a donor, it must be transported, for example to a facility, so that the biopsy can be cultured to generate a tissue system as disclosed herein. It is important that a sufficient portion of the biopsy remain viable during transport so that a tissue system can be derived therefrom. An example of a transport device designed to maintain the viability of cells is disclosed in U.S. Ser. No. 11/385,017, which is incorporated herein by reference. Preferably, the biopsy is transported or stored in a medium which supports the viability of the biopsy. The conjunctival tissue biopsy should be processed as soon as possible after collection. The biopsy may be cultured as either an intact explant, or cut into several pieces or bits before being placed in culture. In preferred embodiments, the presence of an appropriate support material facilitates the binding of the conjunctival cells in the tissue biopsy, thereby facilitating the growth of the conjunctival cells. In one embodiment, after removal from the transport container, the biopsy is placed in PBS. Using fine dissection forceps and a scalpel, the conjunctival biopsy may be cut into multiple small pieces (i.e., explants), for example 0.5 mm in size. The explants may then be placed on the support material for culture, and carefully submerged in culture media. When an amniotic membrane such as HAM is the support material, the explants may be placed on the basement-membrane side of the amniotic membrane. The medium is then changed regularly, being careful not to dislodge the explants. The cells from the explant may be allowed to grow until confluent over the support material, usually after several days in culture.

In preferred embodiments of the above methods for generating a tissue system, the conjunctival tissue is cultured in culture media that supports the growth of conjunctival cells, preferably conjunctival progenitor cells. In preferred embodiments, the isolated conjunctival cells are cultured, expanded and differentiated in a single media, thus avoiding the complex media components and steps involved in media transferring. Preferably the media uses non-carcinogenic, non-irritating ingredients. The media should preferably maintain the viability and proliferation of the conjunctival cells present in the biopsy, as well as the differentiation capacity of progenitor conjunctival cells. The media also preferably supports the preferential growth of conjunctival cells, such as progenitor conjunctival cells. In certain embodiments, the media may also contain factors that promote the differentiation of cells to express an epithelial cell phenotype. The culturing methods disclosed herein for preparing conjunctival tissue systems should omit the use of any feeder cells or feeder layers.

In preferred embodiments, the tissue system of the present disclosure is obtained by using a single medium for culturing, expanding and differentiating conjunctival cells. The procedure disclosed herein for producing the conjunctival tissue system preferably results in a large population of conjunctival cells in the form of a tissue system suitable for transplant. The organized conjunctival tissue equivalent typically comprises conjunctival cells in a multi-layered arrangement, preferably with goblet cells interspersed among the conjunctival cells. Any suitable basic culture media known to those of skill in the art may be used to generate the media for culturing the conjunctival tissue system. The preferred media used for culturing the conjunctival tissue is Dulbecco's Modified Essential Medium (DMEM), DMEM:F-12 (1:1) medium, or Ham's F-12 (1:1) medium, preferably supplemented with a nutrient serum, for example a serum or serum-based solution that supplies nutrients effective for maintaining the growth and viability of the cells (e.g., knock-out serum, heat-inactivated human serum, human cord blood serum, human serum albumin). The preferred percentage of nutrient serum in the media is from about 0.5% to 25%, more preferably from about 15% to 20%.

The media may also be supplemented with growth factors. As used herein, the term "growth factor" refers to proteins that bind to receptors on the cell surface with the primary result of activating cellular proliferation and differentiation. Preferably the growth facilitating agents used to culture the conjunctival cells at any stage are of human or human recombinant origin. The preferred growth factors for culturing conjunctival tissue are selected from epidermal growth factor (EGF) (e.g., human EGF, recombinant human EGF), basic fibroblast growth factor (bFGF), insulin, sodium selenite, or human transferrin, as well as combinations thereof. The preferred concentration of the various growth factors are as follows: (1) about 5 to 15 ng/ml EGF, more preferably about 10 ng/ml EGF, (2) about 2 to 10 ng/ml bFGF, more preferably about 4 ng/ml bFGF, (3) about 1 to 10 µg/ml Insulin, more preferably about 5 µg/ml Insulin, (4) about 1 to 10 µg/ml Transferrin, more preferably about 5 µg/ml Transferrin, (5) about 1 to 10 µg/ml Sodium Selenite, more preferably about 5 µg/ml Sodium Selenite, and (6) about 1 to 10 µg/ml Hydrocortisone, more preferably about 0.5 µg/ml, Hydrocortisone.

Preferably the media further comprises an antibiotic, such as penicillin, streptomycin, or a combination thereof. For the antibiotics used in the media, the antibiotic or mixture of antibiotics preferably comprises about 40 to 60 IU/ml of penicillin, about 40 to 60 µg/ml of streptomycin, 40 to 60 µg/ml of Gentamicin, and/or 40 to 60 ng/ml of Amphotericin B. In certain embodiments, the media comprises 50 U/ml of penicillin-streptomycin. In still further embodiments, the tissues system uses media components which do not include carcinogenic substances, such as cholera toxin and the like, which can cause eye irritation.

In certain embodiments, the culture media may comprise DMEM or DMEM:F-12, further supplemented with a nutrient serum, for example, fetal bovine serum (FBS), human serum albumin, or human cord blood serum. Preferably, the culture medium is supplemented with one or more soluble factors, for example 0.1% dimethyl sulphoxide (DMSO), 10 ng/ml recombinant human epidermal growth factor (rhEGF), 5 µg/ml insulin, 5 µg/ml sodium selenite, 5 µg/ml transferrin, 5 µg/ml hydrocortisone, 4 ng/ml bFGF, and one or more antibiotics. In other embodiments, the media used to prepare the tissue system, including the medium used to transport the conjunctival tissue biopsies, the medium used to culture the biopsies, and the medium used to transport the tissue system, do not contain any sera or other factors of non-human animal origin. This will help minimize any risk of contamination of the tissue system with xenogenic components, thereby making the tissue systems safer for human administration.

In certain embodiments, the conjunctival tissue is cultured on an appropriate support material such as an extracellular matrix or other biocompatible polymers, which may have a biocoated surface, for example extracellular matrix carrier or biocoated petri dishes. Preferably, the extracellular matrix is amniotic membrane, more preferably HAM. The support material may be biocoated with one or more attachment factors, including but not limited to fibrinogen, laminin, collagen IV, tenascin, fibronectin, collagen, bovine pituitary extract, EGF, hepatocyte growth factor, keratinocyte growth factor, hydrocortisone, or any combination thereof. In other embodiments, the support material is placed on nitrocellulose filter paper to facilitate generation of the conjunctival tissue system itself. A nitrocellulose sheet may also provide further support for the conjunctival tissue system. When the support material is amniotic membrane, it may be placed on a nitrocellulose filter paper with the basement-membrane side up. Prior to use, the membrane may be incubated with dispase to help remove any amniotic epithelial cells, which could interfere with the subsequent growth of the conjunctival cells.

Preferably, the support material has characteristics which approximate the natural ocular surface, such characteristics including but not limited to being clear, thin, elastic, biocompatible, non-vascular, and/or non-antigenic. In addition, the support material preferably supports the growth of conjunctival cells, whether progenitor or differentiated conjunctival cells, as well as normal differentiation and/or integration after transplant. In other preferred embodiments, the support material will be gradually resorbed in vivo after transplant of the tissue system. In addition, the support material is preferably non-antigenic.

Amniotic membrane, particularly HAM, is preferred for culturing biopsied conjunctival tissue, and generating the tissue system described herein. Methods for preparing human amniotic membrane are well known to those of skill in the art (see, for example, U.S. Pat. No. 6,152,142, and Tseng et al., (1997) Am. J. Ophthalmol. 124:765-774, each incorporated herein by reference). The amniotic membrane may be used intact with the epithelial surface, or denuded of epithelial cells. For example, amniotic membrane may be prepared to enhance the growth of conjunctival cells by removing endogenous amniotic epithelial cells by freeze-thawing, enzymatic digestion, and/or mechanical scraping, followed by treatment of the surface with growth factors, extracellular matrix compounds, and/or adherence-enhancing molecules. Amniotic membrane is a preferred substrate for generating the tissue system because it is a natural substrate which facilitates the viability and growth of conjunctival cells. In one embodiment, the amniotic membrane, with the basement membrane or stromal side up, is affixed smoothly onto a culture plate for culturing conjunctival cells. Biocompatible membranes are chosen from materials which can adhere to the eye and aid in presenting the cultured cells.

In other embodiments, the conjunctival tissue system is cultured on an appropriate support material such as a tissue base to generate the tissue system. In preferred embodiments, the tissue base is mammalian amniotic membrane, Matrigel™, laminin, collagen IV or collagen IV sheet, tenascin, fibrinogen, fibronectin, and fibrinogen and thrombin sheet (Fibrin Sealant, Reliseal™), or any combinations thereof. The tissue base may also be biocoated with a support material, including but not limited to human amniotic membrane, laminin, collagen IV, tenascin, fibrinogen, thrombin, fibronectin, or combinations thereof. In certain preferred embodiments, the tissue base is human amniotic membrane, more preferably biocoated human amniotic membrane. The conjunctival tissue is preferably cultured in medium that will allow the cells to expand without substantially differentiating, for example in culture medium supplemented with a nutrient serum and/or one or more soluble growth factors.

In some embodiments, the conjunctival cells cultured on an appropriate support material may be dissociated from the support material to isolate progenitor conjunctival cells. In other embodiments, the conjunctival cells are sorted using methods well known to those of skill in the art, for example magnetic-affinity cell sorting (MACS), or fluorescence-activated cell sorting (FACS), or immuno-labeling or immuno-fluorescence-staining techniques (such as solid phase adsorption), to isolate a population of conjunctival progenitor cells and/or differentiated conjunctival cells, either before or after culturing on a suitable support material. In embodiments that isolate populations of conjunctival cells enriched using one of the above methods, the isolated cells are preferably cultured under conditions and in a media that supports the growth of progenitor cells and the development of a tissue system for transplanting onto a damaged or diseased eye.

Preferably the tissue comprising conjunctival cells is cultured for 10-20 days, more preferably 12-14 days, to generate the conjunctival tissue system. The cells may be cultured under conditions well known to those of skill in the art, for example under submerged or air-lifted conditions. Preferably the tissue system cultured under these conditions will comprise at least about 30%, 40%, 50%, 60%, 70%, 80%, 90%, or 95% progenitor conjunctival cells. In a preferred embodiment, the isolated progenitor conjunctival cells are cultured on a support material in the presence of an enriched medium for developing the tissue system with progenitor conjunctival cells. Preferably, the tis support material has characteristics which approximate the natural conjunctival tissue and can also support the growth of progenitor conjunctival cells, as well as normal differentiation after transplant. After the tissue system disclosed herein is generated, it must be transported to the recipient's location for transplant. Preferably, the means used to transport the tissue system maintains the viability of the tissue system sufficiently that it is still useful as a transplant after transport.

Preferably the tissue system is transplanted onto a damaged or diseased eye and able to repair ocular surface impairments, particularly in subjects with severe conjunctival damage or disease. As used herein, a subject with severe conjunctival damage or disease may have a complete absence of conjunctival progenitor cells in the damaged or diseased eye. The conjunctival tissue system may be transplanted to replace or support the ocular surface at any location, including areas that are adjacent to the cornea. In preferred embodiments, the conjunctival tissue system is transplanted to the sclera, forniceal or tarsal areas of the optical surface. The conjunctival tissue system also may be placed with existing conjunctiva on the inner surface of the eyelid.

A variety of surgical approaches that are well known to those of skill in the art have evolved to select, harvest, and transport ocular tissue equivalents to their appropriate, natural anatomic niche at the recipient eye. Prior to transplant, the diseased or damaged conjunctiva may be excised, with the autologous or heterologous conjunctival tissue system placed over the conjunctival defects. The transplant of the conjunctival tissue system is carried out under aseptic conditions, as well as under local anesthetic. Another transplant may also be placed over the conjunctival tissue system, for example an additional amniotic membrane patch graft, to act as a protective patch. In other embodiments, a contact lens may be placed over the tissue system to protect the transplant. Surgical methods for transplanting a tissue system to the eye of a recipient are well known to those of skill in the art (Nguyen et al., J Pediatr Ophthalmol Strabismus, 44(1):35-38, 2007; Bahar et al., Cornea 25(10):1168-1172, 2006). A wide array of sutures and suturing techniques, which are well known to those of skill in the art, may be used to affix transplants to the ocular surface. Although generally successful, suturing thin tissues to the ocular tissues creates special problems related to tissue-to-tissue apposition, hemorrhage, inflammation, visualization, and the discomfort of the patient from exposed sutures on the ocular surface. The goal of achieving optimal tissue apposition, using biologically suitable products without sutures, is highly desirable. In addition, reduced time in surgery translates to less facility costs.

While appropriate tissue systems are needed to help repair ocular injuries or conditions, there is also a need to reduce or replace sutures in a variety of ophthalmic procedures to improve outcomes, minimize complications, provide patient comfort, and shorten procedure lengths. Thus, in certain embodiments, the present disclosure provides for a sutureless delivery of a tissue system to the eye of a patient. The process involves the use of a biocompatible adhesive such as glue, for example amcrylate or fibrin sealant, which can be used as a tissue adhesive. The technique can be used for the delivery of corneal as well as conjunctival cells to damaged or diseased eyes. The suture-less delivery of a tissue system disclosed herein may also be used with a tissue system comprising undifferentiated stem cells derived from corneal limbus, as disclosed in U.S. Ser. No. 11/043,019, which is incorporated herein by reference in its entirety. In preferred embodiments, the present disclosure provides for the delivery of the tissue system comprising conjunctival cells using a amcrylate. In other preferred embodiments, the biocompatible adhesive is a sterile tissue adhesive selected from polylactic acid, polylactide glycolic acid, copolymers of polylactic acid and acrylates, or any combinations thereof. In still other embodiments, the biocompatible adhesive comprises any adhesive which is biocompatible with the eyes and is neater, safer, and less cumbersome than sutures, so that the cultured tissue system may be set on the injury while minimizing the disturbance to the recipient's eye. Preferably, the use of an adhesive with the tissue system facilitates integration of the transplanted cells with the damaged or diseased eye.

The conjunctival tissue system disclosed herein can be utilized for therapeutic applications, for example as a transplant for subjects in need of treatment. The tissue system of the present disclosure can be used to treat any subject in need of treatment, including but not limited to humans, primates, and domestic, farm, pet, or sports animals, such as dogs, horses, cats, sheep, pigs, cattle, rats, mice, and the like. As used herein, the terms "therapeutic," "therapeutically," "to treat," "treatment," or "therapy" refer to both therapeutic treatment and prophylactic or preventative measures. Therapeutic treatment includes but is not limited to reducing or eliminating the symptoms of a particular disease, condition, damage, injury or disorder, or slowing or attenuating the progression of, or curing an existing disease, condition, damage, injury or disorder. Preferably, subjects in need of such therapy will be treated with a therapeutically effective amount of the conjunctival tissue system to restore or regenerate function. As used herein, a "therapeutically effective amount" of the conjunctival tissue system is an amount sufficient to arrest or ameliorate the physiological effects in a subject caused by the loss, damage, malfunction, or degeneration of conjunctival cells or tissue.

The therapeutically effective amount of the tissue system used will depend on a variety of factors well known to those of skill in the art, such as the needs of the subject, the subject's age, physiological condition and health, the desired therapeutic effect, the size of the area of tissue that is to be targeted for therapy, the site of implantation, the extent of pathology, the chosen route of delivery, and the treatment strategy. Those of skill in the art will be able to use these factors to determine the therapeutically effective amount of the tissue system disclosed herein needed to treat the patient. The tissue system is preferably administered to a patient in a manner that permits the tissue system to graft to the intended site and reconstitute or regenerate the functionally deficient area.

In a particular embodiment, the present disclosure relates to culturing human forniceal conjunctival progenitor and/or differentiated cells on HAM in an atypical and simple culture scheme using glass slides. The prepared tissue system was characterized and assessed for safety on a rabbit model of ocular conjunctival burn injury, which did not involve suturing. The viable and functional engrafted human cells derived from the conjunctiva were traced in this rabbit model. See Examples 1 and 2. As described herein, the safety of the tissue system in terms of abnormal vascularisation underneath the graft, and polymorphonuclear leukocytes (PMN) infiltration, was compared in parallel with controls. The severe bilateral destruction of conjunctival epithelium may be treated by engraftment of cultures of conjunctival epithelium with goblet cells propagated from the fornix or other zones of the conjunctiva. Shatos et al., IOVS 44(6):2477-2486, 2003; Zieske, Eye 8:163-169, 1994; Tsai et al., Prog Retinal Eye Res 16:227-241, 1997.

The following examples are included to demonstrate preferred embodiments of the disclosure. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation of a Conjunctival Tissue System.

The process of culturing conjunctival cells from a tissue biopsy as disclosed in this Example is very simple and different from the existing millicell method. See Pellegrini et al., J. Cell Biol 145(4):769-782, 1999; Belyakov et al., Proc. Natl. Acad. Sci USA 102(40):14203-208, 2005. With the approval of an ethics committee, the collection of the conjunctival biopsies was done with prior informed consent of each patient and donor. The protocols followed were according to the tenets of the Declaration of Helsinki, and were approved by the Reliance Life Sciences (RLS) ethics committee. About 2 $mm^2$ of human conjunctival tissue was surgically removed from the fornix during periocular surgery a the Zee Eye clinic, Bandra, Mumbai, India. The conjunctiva was collected carefully only from the periphery of the eyeball and on the inner surface of the eyelid. The excised tissue was then immediately placed in a transport medium consisting of Dulbecco's Modified Eagles Medium (DMEM), 5% heat inactivated Fetal Bovine Serum (Hyclone USA), and 50 µg/ml penicillin-streptomycin. The pH of the transport medium was in the range of 7-7.4. The biopsies were stored at 4° C. until they were cultured.

Blood samples of about 2-5 ml from the same patient who had provided the tissue biopsy were collected and transported along with each conjunctival biopsy to a centrally located cGMP facility. Blood samples were immediately tested for infectious diseases, including Hepatitis B virus (HBV), Hepatitis C virus (HCV), Syphilis and CMV.

The biopsies were then placed on an appropriate matrix for culturing conjunctival cells in the biopsy. This matrix, Human Amniotic Membrane (HAM), was prepared as follows. With proper informed consent of the donor, and in accordance with the tenets of the Declaration of Helsinki, human placenta was obtained from Sero negative donors at the time of cesarean section. The method used to isolate HAM was similar to that described by Tseng et al., Arch Ophthalmol. 116:431-41, 1998, which is incorporated herein by reference. The processed HAM was cut into 5×5 $cm^2$ after spreading on a sterile nitrocellulose membrane. The cut pieces were stored in DMEM containing glycerol and FBS at −70° C. until use. The sterility of the storage medium was checked on the day of the preparation and on the 14th day of cold storage. Before use, HAM was thawed and treated with a 0.5% Trypsin-EDTA (Gibco-BRL, USA) solution for denuding, and stretched on a 5×5 cm² sterile glass slide that was kept in a sterile petri plate with sufficient medium added to it.

To culture and expand conjunctival progenitors cells, the epithelium of the conjunctival biopsied tissue first was separated from the underlying stroma (almost completely) under the stereomicroscope. The epithelial segment was finely cut into 10 small bits and placed on the denuded and stretched HAM after preincubation with PBS and 25 U/ml Pen-Strep (Giboc-BRL, USA). The bits of biopsy comprising conjunctival cells were placed in a concentric ring manner on the HAM, allowing the cells to stratify by contact inhibition. On day zero, the biopsy tissue was covered with 750 µl of culture medium consisting of DMEM:F12 (1:1), 20% Fetal bovine Serum, (hyclone, Logan Utah), 0.1% DMSO (Sigma USA), 10 ng/ml human Epidermal Growth Factor (hEGF) (Sigma USA), 4 ng/ml basic Fibroblast Growth Factor (bFGF) (R&D MN), 5 µg/ml of Insulin (Sigma USA), Transferrin (Giboc-BRL, USA) and Sodium Selenite (Sigma USA) each, 0.5 µg/ml, Hydrocortisone (Sigma USA) and 50 U/ml Pen-Strep. On day two, 2.5 ml of the culture medium was added to the set up, and the medium was changed every alternate days thereafter until ready for transplant. The cells were grown at 37° C. with 5% $CO_2$. This single culture media was used to prepare the tissue system.

It was surprising that a method which uses the same single-step media for the proliferation and differentiation of the conjunctival cells could successfully produce a tissue system for transplant, given the structural characteristics necessary for such a tissue system with the combination of single step media, this media maintains the proliferation and differentiation. The present invention has achieved a proliferative and differentiated cells in the same culture. Insulin, hEGF and hydrocortisone all function to promote the growth of conjunctival epithelial cells over the fibroblasts during the culturing process. After 14 days of culture, the entire stretch of amniotic membrane was covered and confluent with cells.

Of the 5×5 cm² stretch of cultured conjunctival tissue system, half was used as a xeno-transplant on a rabbit model of conjunctival injury as described in Example 2, and half was cut into three pieces. One piece was used to collect the RNA from cells for RT-PCR so that expression of certain markers could be measured and evaluated. A second piece was prepared for sectioning in a paraffin block. And the last piece was prepared as a whole mount.

RNA isolation and RT-PCR: Total RNA from the cultured conjunctival cells was isolated by the TRIzol method (Invitrogen, USA), and 1 µg of isolated RNA was treated with RNase-OUT ribonuclease inhibitor (Invitrogen, USA) for cDNA synthesis. Reverse-transcription was carried out using Superscript reverse-transcriptase II (Invitrogen, USA) and Oligo dT (Invitrogen, USA) to prime the reaction. RT-PCR of the cells was done with MUC5AC and MUC4 genes to confirm expression of mucin. 2 µl of cDNA was amplified by polymerase chain reaction for 30 cycles using Abgene 2×PCR master mix (Abgene, USA) and appropriate primers (Shatos et al., IOVS 42(7):1455-1464, 2001; Shatos et al., IOVS 44(6):2477-2486, 2003; each of which is incorporated herein by reference). The primer sequences used in this reaction are shown below in Table 1.

TABLE 1

| Gene | Primer sequence | Annealing temperature | Function |
|---|---|---|---|
| GAPDH | Forward-5'ACC ACA GTC CAT GCC ATC AC 3' (SEQ ID NO:1) Reverse-5'TCC ACC ACC CTG TTG CTG TA 3' (SEQ ID NO:2) | 60° C. | House keeping gene |
| MUC5AC | Forward-5'TCC ACC ATA TAC CGC CAC AGA 3' (SEQ ID NO:3) Reverse-5'TGG ACG GAC AGT CAC TGT CAA C 3' (SEQ ID NO:4) | 65.9° C. | Human conjunctival goblet cells specifically express this large gel-forming mucin |
| MUC4 | Forward-5'GCC CAA GCT ACA GTG TGA CTC A 3' (SEQ ID NO:5) Reverse-5'ATG GTG CCG TTG TAA TTT GTT GT 3' (SEQ ID NO:6) | 66.6° C. | Membrane associated mucin |

Preparation of conjunctival culture whole mount: The tissue system piece comprising cultured conjunctival cells was stretched out on a cut glass slide without disturbing the surface. Traces of culture medium were removed, and the sample was fixed in formaldehyde for 30 minutes at room temperature. Subsequently, the fixed culture was completely air dried and stained.

Histolabeling and Histopathology: To determine the characteristics of the tissue system, the composite cell cultures were fixed in 4% paraformaldehyde at room temperature for 10 minutes and were dehydrated and paraffin embedded. Approximately 3-µm paraffin sections were prepared. For immunofluorescence, after deparaffinisation, the sections were subjected to a microwave method of antigen retrieval and preincubated with 1×PBS for 10 minutes. The sections were treated with 0.2% Triton X-100 for 5 minutes and blocked with 1% BSA for 1 hour with intermediate washing with PBS for 15 minutes. Primary antibodies AE-1 (1:500) and AE-3 (1:500) (Chemicon, Calif.) were added to the sections and incubated overnight at 4° C. Sections were incubated with respective secondary antibodies for 1 hour at room temperature. Sections were mounted with mounting media (Sigma US) and examined with a fluorescent microscope. For Periodic Acid Schiff (PAS) staining, deparaffinised sections along with the whole mount were treated with 0.5% Periodic acid for 5 minutes and Schiff reagent for 30 minutes at room temperature. The sections were counter stained with hematoxylin.

Figure 2:
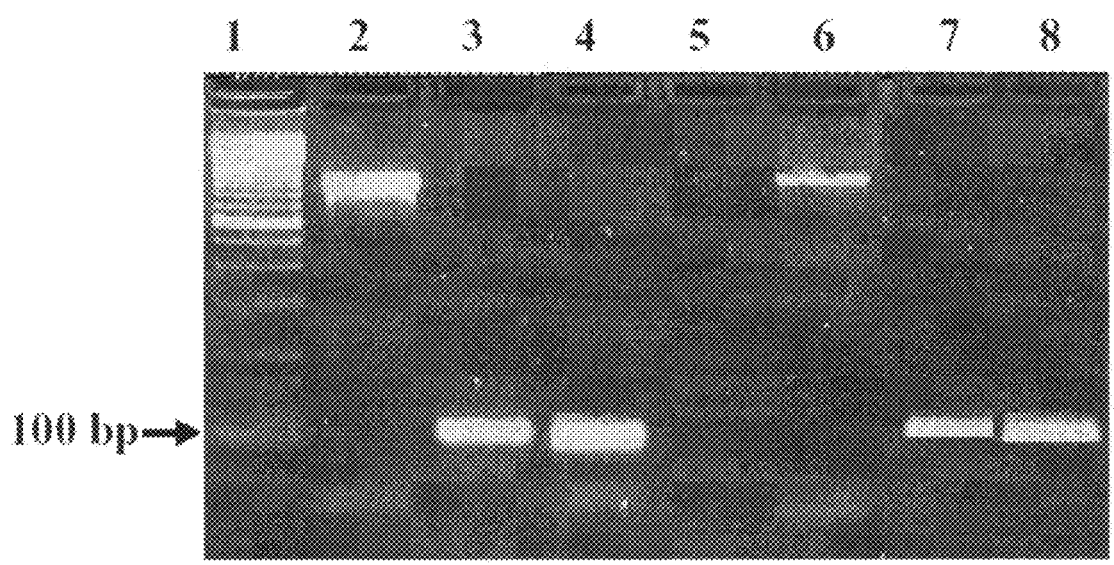
FIG. 2: Expression of MUC5AC and MUC4 in the conjunctival tissue system and conjunctival biopsy. RT-PCR analysis of conjunctival cultured cells and conjunctival biopsy with MUC5AC (103 bp) (lanes 3, 7) and MUC4 (102 bp) (lanes 4, 8) markers, respectively. Lane 1 is a 1 Kb DNA size marker; lanes 2 and 6 are GAPDH (house keeping gene) of cultured conjunctival cells and conjunctival biopsy, respectively. Lane 5 is a negative control with no cDNA added to the reaction mixture.

Characterizing the cultured conjunctival cells on denuded amniotic membrane: As shown herein, markers for cytokeratins and specific mucin types (Ohno-Matsui et al., Molecular Vision 11:1-10, 2005) were identified as being expressed by the cultured conjunctival cells. Prior to transplant, the conjunctival tissue system was stratified in vitro. The primary culture showed the initiation of growth in a three-day-old culture after the biopsy was placed on HAM, with large cells coming out of the explants on the amniotic membrane (FIG. 1A). After 14 days of culture, the entire stretch of HAM was covered and confluent with cells (FIG. 1B). After 20 days of culture, immunofluorescence staining of the culture sections demonstrated cytoplasmic expression of AE-1 and AE-3 (FIGS. 1C and 1D). PAS staining of the conjunctival tissue system whole mount prepared at the end of 20 days showed the growth and distribution of goblet cells, which were not uniformly found in the tissue system (FIG. 1E). The complementary RT-PCR analysis to detect expression of MUC5AC and MUC4 in the conjunctival tissue system confirmed expression of these two markers in the tissue system, as well as in the conjunctival biopsy (FIG. 2). As described in Example 2 below, the transplanted conjunctival tissue system was able to treat a conjunctival injury.

Example 2

The present Example examines the ability of the conjunctival tissue system prepared using a plain culture scheme as described in Example 1 to treat the injured eye of a rabbit model of ocular conjunctival burn injury xeno-transplanted with the tissue system. The conjunctival tissue system was grafted using a tissue adhesive in the rabbit model. After transplantation, the survival and integration of the human cells were traced and evaluated using histopathology and immunostaining. The safety of the conjunctival tissue system in terms of abnormal vascularisation underneath, as well as polymorphonuclear leukocytes (PMN) infiltration, was checked in parallel with controls.

Figure 3:
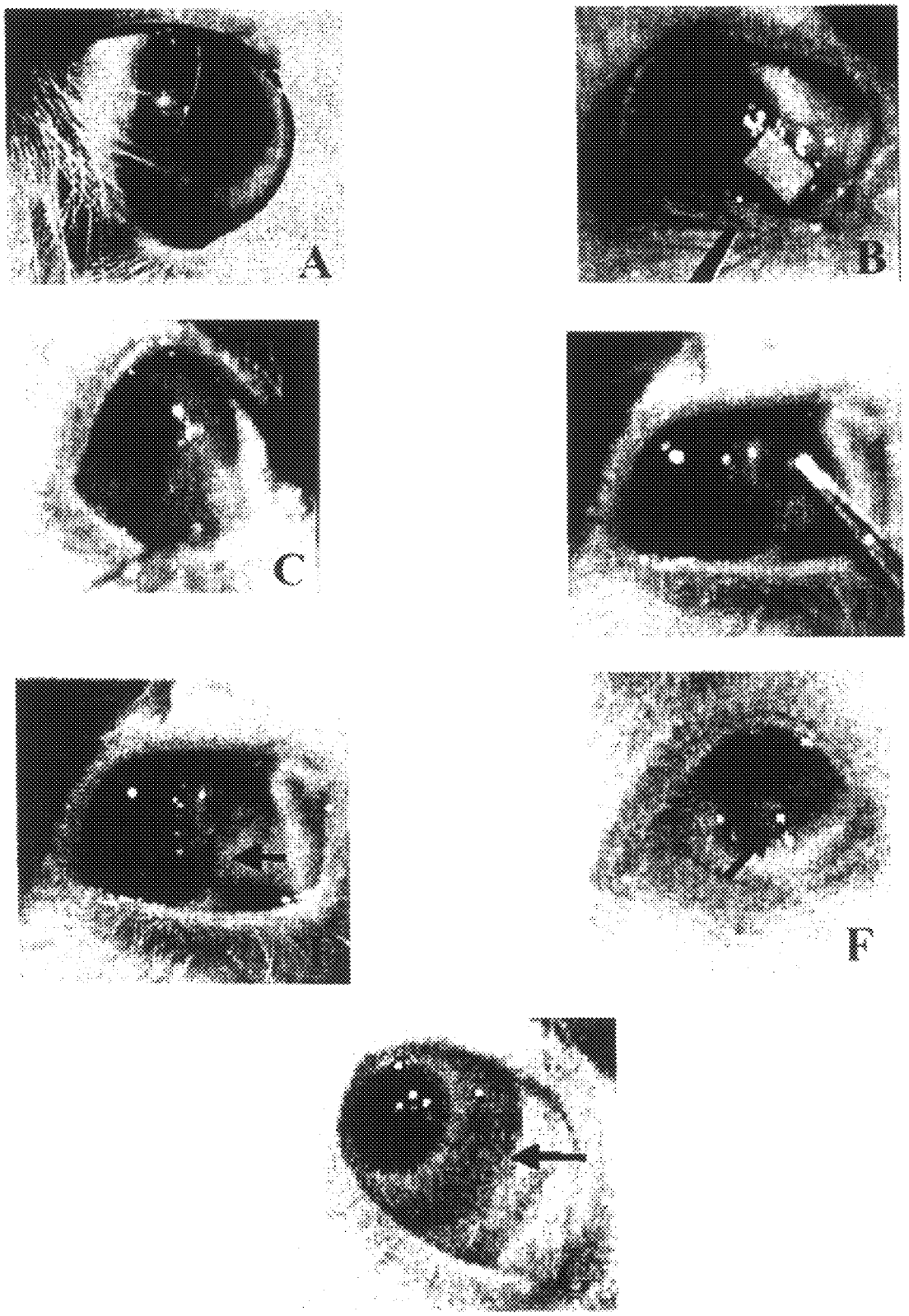
FIG. 3: Rabbit model of chemical injury creation and transplantation showing the injury, transplantation and healing.

The rabbit model of chemical injury was prepared as follows. Prior approval of the internal review board (IRB), Institutional Animal Ethics Committee (IAEC), and Committee for the Purpose of Control and Supervision of Experiments on Animals (CPCSEA) was obtained for the animal protocols as described herein. Six New Zealand white Rabbits (weight: 1.5 kg; age: 6 months) were anaesthetized with ketamine (35 mg/kg) and xylazine (5 mg/kg), and the eye lids were retracted by the application of stay sutures. FIG. 3A shows a rabbit's normal eye. The injury on bulbo-palpebral conjunctiva was made by placing a sterile filter paper (60 $mm^2$) saturated with 1N NaOH, for 40 seconds on that location of the eye (FIG. 3B). After removal of the filter paper, the residual epithelium at the injured zone was removed by surgical blade and the wound site was liberally irrigated with PBS. Injury was created in one eye of the animal. The method to generate the injury was done again on the same area after 15 days, and followed for 10 additional days as before.

For the xeno-transplantation experiment, there were two types of controls. One control was an animal in which the eye was injured and followed up for 45 days (n=2). The second control was an animal in which the eye was injured (FIG. 3C), and then covered with HAM without cultured conjunctival cells on it (n=2). The test experiment transplanted the human conjunctival tissue system as described herein on the injury (FIGS. 3D and 3E). The injury was covered with a 20 mm piece of a conjunctival tissue system with cultured cells facing upward, and edges were fixed using the sterile tissue adhesive called Amcrylate (manufactured in India by Concord Drugs Ltd, Andhra Pradesh). This polymer is isoamyl 2-cyanoacrylate, a monomer which, when in contact with moisture, polymerizes, and has been shown to be a non-toxic, biocompatible, and inert material. This tissue adhesive was used for adhering the transplant on the bare conjunctival tissue. Four 5 µl drops of the tissue adhesive were place on the four edges of the injury, and the transplant was placed in such a way that the HAM was placed in touch with the glue and the cells were facing up.

Each eye was treated with a dexamethazone/gentamycin solution twice a day for 15 days after the injury was made. After surgery 0.5% cyclosporin A and 0.05% dexamethazone-gentamycin solution were given as ocular drops three times a day during the first week and twice daily thereafter. Animals were followed up for a one-month period. The efficiency of the transplant was quantified by re-epithelisation and reappearance of goblet cells at the site of injury in comparison to the control animals.

At the end of the animal experiment, rabbits were sacrificed and whole eye ball with conjunctival tissues were removed and fixed in 10% formalin. Rabbits were sacrificed using a dosage of thiopentone sodium solution by intracardiac injection. For histopathological evaluation, conjunctival tissues from control and treatment sites were processed routinely, with thin sections of ~5 microns stained with hematoxylene and eosin stain and observed microscopically for the extent of repair. For Immunohistochemistry, after the sections were subjected to antigen retrieval, they were treated with 3% $H_2O_2$ in water for 15 minutes. Primary antibody anti-human mitochondrial antibody (Chemicon, CA) incubation was carried overnight at 4° C. The rest of the procedure for staining was according to the instructions of the VectaStain Elite ABC kit (Vector Laboratories, Burlingame, Calif.) used. The substrate used was Diaminobenzidine (DAB). The brown colored spaghetti-like positive staining pattern in the cytoplasm of the human cells was visualized by light microscopy (Nikon E600). For Periodic Acid Schiff staining, deparaffinised sections along with the whole mount were treated with 0.5% Periodic acid for 5 minutes and Schiffreagent for 30 minutes at room temperature. The sections were counter stained with hematoxylin.

Clinical observations post injury and transplantation: 24 hours after injury, all eyes showed slight congestion around the injury site and a blood clot on the site of the injury. After 48 hours the size of the blood clot decreased (data not shown), the congestion decreased, and the site of injury could be demarcated. There were no allergic reactions observed following transplantation of the conjunctival tissue system and no signs of rejection. The eyes were calm and no abnormal vascularisation was observed during the follow up period. The eye with only injury was followed up until the day of termination of the experiment, and showed two-thirds of the original injury created (FIG. 3F). The eye transplanted with the tissue system comprising conjunctival human cells looked healthy in terms of surface integrity and vascularisation at the site just before sacrificing the animal for sectioning (FIG. 3G).

Figure 4:
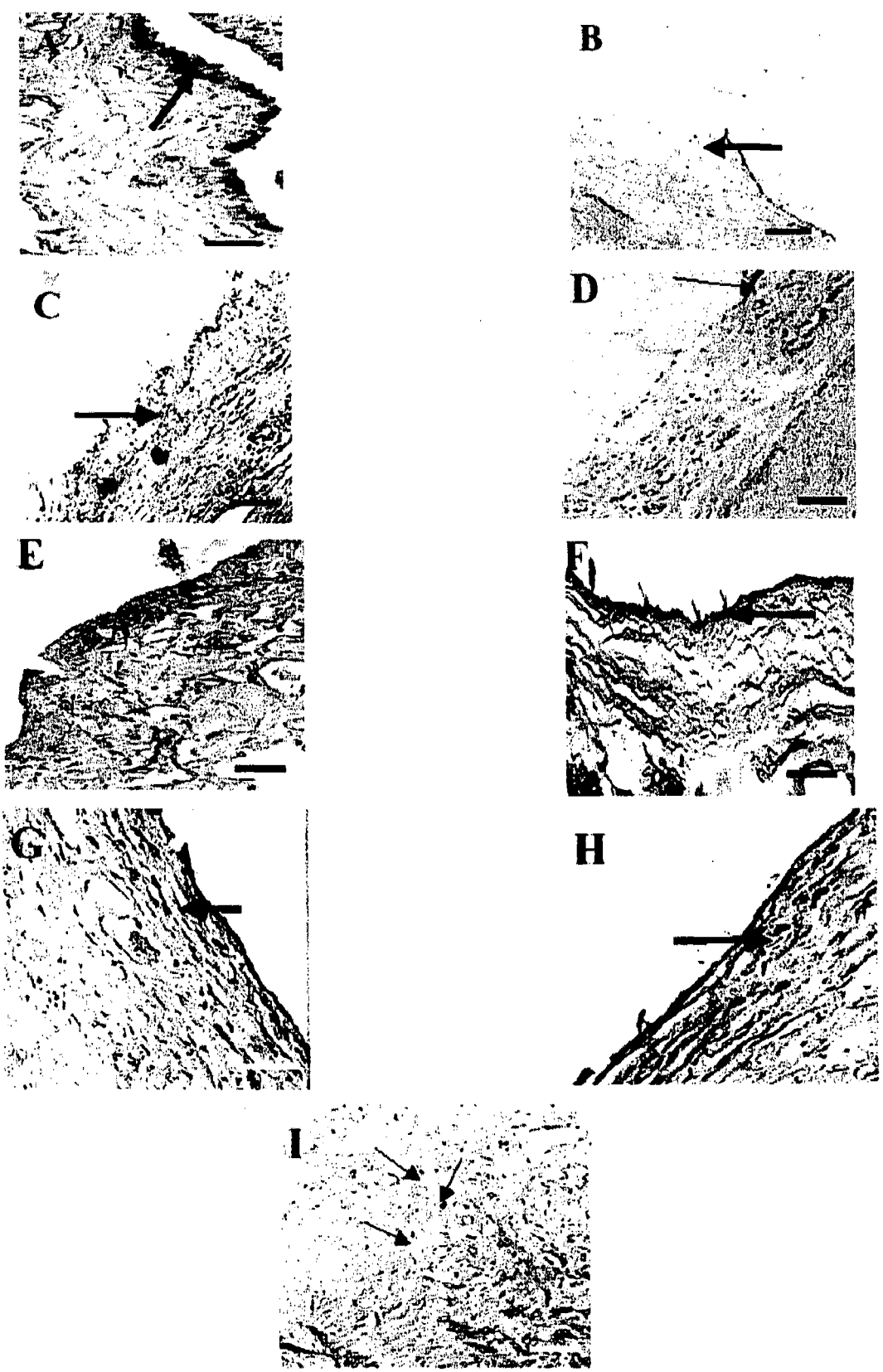
FIG. 4: Evaluating the effect of transplantation on injury and detecting the retained and survived human cells in vivo.

In order to assess the ability of the conjunctival tissue system to heal the injured eye in the rabbit model, the eyes were compared to a normal rabbit conjunctiva section, which has a healthy population of goblet cells, as shown in FIG. 4A. After injury, no goblet cells are found at the sight of injury, and the epithelium is sloughed off (FIG. 4B). In addition, sections from control animals with only injury showed distorted epithelial cells and congested blood vessels with mild infiltration of PMN. In control rabbits in which only denuded HAM was transplanted at the site of injury, epithelium did not regenerate, and was sloughed off in the majority of the area (FIG. 4C). There were no traces of goblet cells at the site and blood vessels were engorged, and extravasated RBCs were seen at many places. In control rabbits that received no transplant, extravasated RBCs also were seen at many places (FIG. 4D). Before transplantation, the conjunctival tissue system was shown to be stratified in vitro. One month after transplantation of the tissue system into the rabbit model, the cells were found intact at the site of application, but not continuous (FIGS. 4E and 4F). Sections from the test eyes, in which the conjunctival tissue system was transplanted, revealed multi-layered epithelium with both human and rabbit cells interspersed. The reappearance of goblet cells and scattered endothelial cells indicate regeneration and healing of the cells at the site of injury.

Detecting the retained and survived human cells in vivo: The human cells transplanted were identified both on the HAM of the tissue system in situ, and embedded in the sub-epithelial zone of the rat model transplanted with the conjunctival tissue system (FIG. 4I). The observation of human cells interspersed at the site of transplant, as well as the migration of the cells inside the animal tissue away from HAM, suggests that they play an important role in healing the injury. Human cells were detected based on the brown colored spaghetti-like staining of human mitochondria with anti-human mitochondrial primary antibody. The percentage of migrated cells varied from animal to animal, with no consistent levels of migration observed. The retained human cells were elongated and big compared to the animal cells, and quite distinct.

The suture-less delivery of the conjunctival tissue system performed using the sterile tissue adhesive Amcrylate demonstrated the safety and convenience of this method. This sterile tissue adhesive does not get absorbed into the blood stream, and has been used to replace or supplement sutures in cosmetic surgery to rejoin veins and arteries. After transplantation, examination under the microscope indicated that there were no traces of the glue underneath the HAM segment in the rabbit's conjunctival sections, suggesting that the glue must have been washed off during the integration of the transplant. The safety of both the transplant and the tissue adhesive were examined by observing PMN infiltration and any induced abnormal vascularisation after transplantation. The results of the histopathological evaluation of sections made from tissues isolated is shown below in Table 2.

TABLE 2

| INJURY ONLY | INJURY WITH HAM TRANSPLANT | INJURY WITH CONJUNCTIVAL TISSUE SYSTEM |
| --- | --- | --- |
| Distorted epithelial cells | Epithelium is sloughed off from majority of area | Multilayered epithelium |
| No goblet cells were seen | No goblet cells were seen | Reappearance of goblet cells |
| Congested blood vessels with infiltration of PMN cells | Blood vessels were engorged and extravasated RBCs were seen at many places | Focal accumulation of PMN cells under epithelial lining with endothelial cells |

While the fundamental novel features of the conjunctival tissue system disclosed herein have been described, it will be understood that various omissions, substitutions and changes in the form and details may be possible without departing from the spirit of the present disclosure. For example, it is expressly intended that all combinations of those elements and/or method steps, which perform substantially the same function in substantially the same way to achieve the same results, are within the scope of the present disclosure.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for generating a conjunctival tissue system consisting essentially of obtaining a conjunctival biopsy obtained from the fornix region of the conjunctiva, the conjunctival biopsy comprising a stroma segment and an epithelial segment, removing the stroma segment of the conjunctival biopsy, and culturing the epithelial segment of the conjunctival biopsy on a support material in a single medium comprising:
   (a) Dulbecco's Modified Essential Medium (DMEM), DMEM:F-12 (1:1) medium, or Ham's F-12 (1:1) medium;
   (b) a nutrient serum selected from the group consisting of knock-out serum, heat-inactivated human serum, human cord blood serum, human serum albumin, and fetal bovine serum;
   (c) epidermal growth factor (EGF);
   (d) basic fibroblast growth factor (bFGF);
   (e) insulin;
   (f) sodium selenite;
   (g) transferrin; and
   (h) an antibiotic or mixture of antibiotics,
   wherein the single medium supports the culture and differentiation of the conjunctival biopsy on the support material to form a conjunctival tissue system.

2. The method of claim 1, wherein the nutrient serum is knock-out serum.

3. The method of claim 1, wherein the nutrient serum is heat-inactivated human serum, human cord blood serum, or human serum albumin.

4. The method of claim 1, wherein the EGF is human EGF or recombinant human EGF.

5. The method of claim 1, wherein the transferrin is human transferrin.

6. The method of claim 1, wherein the single medium further comprises dimethyl sulphoxide.

7. The method of claim 1, wherein the single medium comprises:
   (a) 15% to 20% nutrient serum;
   (b) 5 to 1 ng/ml EGF;
   (c) 2 to 10 ng/ml bFGF;
   (d) 1 to 10 µg/ml insulin;
   (e) 1 to 10 µg/ml sodium selenite; and
   (f) 1 to 10 µg/ml transferrin.

8. The method of claim 7, wherein the single medium comprises:
   (a) 20% nutrient serum;
   (b) 10 ng/ml EGF;
   (c) 4 ng/ml bFGF;

(d) 5 µg/ml insulin;
(e) 5 µg/ml sodium selenite; and
(f) 5 µg/ml transferrin.

9. The method of claim 8, wherein the single medium further comprises 0.1% dimethyl sulphoxide.

10. The method of claim 1, wherein the support material is a biocompatible membrane.

11. The method of claim 10, wherein the biocompatible material is amniotic membrane.

12. The method of claim 11, wherein the amniotic membrane is human amniotic membrane.

13. The method of claim 11, wherein the culturing step is performed on the surface of a basement membrane side of the amniotic membrane.

14. The method of claim 1, wherein the culturing step is performed without feeder cells.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer sequence

<400> SEQUENCE: 1
accacagtcc atgccatcac                                             20

<210> SEQ ID NO 2
<211> LENGTH: 20
<212> TYPE: DNA
<213> ORGANISM: Artificial Sequence
<220> FEATURE:
<223> OTHER INFORMATION: Primer sequence

<400> SEQUENCE: 2
tccaccaccc tgttgctgta                                             20

```
<210> SEQ ID NO 3
<211> LENGTH: 21
<212> TYPE: DNA
<213> ORGANISM: Artificial Sequence
<220> FEATURE:
<223> OTHER INFORMATION: Primer sequence

<400> SEQUENCE: 3
tccaccatat accgccacag a                                             21

<210> SEQ ID NO 4
<211> LENGTH: 21
<212> TYPE: DNA
<213> ORGANISM: Artificial Sequence
<220> FEATURE:
<223> OTHER INFORMATION: Primer sequence

<400> SEQUENCE: 4
tccaccatat accgccacag a                                             21

<210> SEQ ID NO 5
<211> LENGTH: 22
<212> TYPE: DNA
<213> ORGANISM: Artificial Sequence
<220> FEATURE:
<223> OTHER INFORMATION: Primer sequence

<400> SEQUENCE: 5
gcccaagcta cagtgtgact ca                                            22

<210> SEQ ID NO 6
<211> LENGTH: 23
<212> TYPE: DNA
<213> ORGANISM: Artificial Sequence
<220> FEATURE:
<223> OTHER INFORMATION: Primer sequence

<400> SEQUENCE: 6
atggtgccgt tgtaatttgt tgt                                           23
```